United States Patent [19]

Fukuoka et al.

[11] Patent Number: 5,187,289

[45] Date of Patent: Feb. 16, 1993

[54] METHOD OF PREPARING 2-PHENYL BENZOTRIAZOLES

[75] Inventors: Naohiko Fukuoka, Kobe; Kazunobu Kubota, Tatsuno; Kunitoshi Iguchi, Osaka, all of Japan

[73] Assignee: Chemipro Kasei Kaisha, Ltd., Hyogo, Japan

[21] Appl. No.: 740,868

[22] Filed: Jul. 31, 1991

Related U.S. Application Data

[63] Continuation of Ser. No. 561,354, Aug. 1, 1990, abandoned, which is a continuation of Ser. No. 320,992, Mar. 9, 1989, abandoned.

[30] Foreign Application Priority Data

Jan. 31, 1989 [JP] Japan ................... 1-22225

[51] Int. Cl.$^5$ ................................. C07D 249/18
[52] U.S. Cl. ..................... 548/260; 548/257; 548/259
[58] Field of Search ............ 548/257, 259, 260

[56] References Cited

U.S. PATENT DOCUMENTS

| Re. 29,586 | 3/1978 | Strobel | 548/260 |
|---|---|---|---|
| 3,978,074 | 8/1976 | Jancis et al. | 548/259 |
| 4,230,867 | 10/1980 | Kintopf | 548/260 |
| 4,383,863 | 5/1983 | Dexter | 548/260 |
| 4,727,158 | 2/1988 | Seltzer | 547/257 |
| 4,785,063 | 11/1988 | Slongo | 548/260 |
| 4,943,637 | 7/1990 | Seino | 548/260 |
| 4,999,433 | 3/1991 | Prestel | 548/260 |
| 5,104,992 | 4/1992 | Fukuoka et al. | 548/260 |

FOREIGN PATENT DOCUMENTS

| 1073463 | 3/1980 | Canada | 548/260 |
|---|---|---|---|
| 0363318 | 4/1990 | European Pat. Off. | 548/260 |
| 380839 | 8/1990 | European Pat. Off. | 548/260 |
| 52-113973 | 9/1977 | Japan | 548/260 |
| 52-113974 | 9/1977 | Japan | 548/260 |
| 59-170172 | 9/1984 | Japan | . |

*Primary Examiner*—Donald G. Daus
*Attorney, Agent, or Firm*—Felfe & Lynch

[57] ABSTRACT

A method of preparing 2-phenylbenzotriazoles expressed by Formula I:

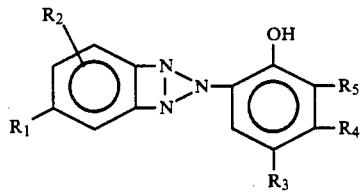

(wherein $R_1$ denotes a hydrogen or chlorine atom, a lower alkyl group having 1 to 4 carbon atoms, a lower alkoxyl group having 1 to 4 carbon atoms, a carboxyl group or a sulfonic acid group; $R_2$ denotes a hydrogen or chlorine atom, a lower alkyl group having 1 to 4 carbon atoms or a lower alkoxyl group having 1 to 4 carbon atoms; $R_3$ denotes a hydrogen or chlorine atom, an alkyl group having 1 to 12 carbon atoms, a lower alkoxyl group having 1 to 4 carbon atoms, a phenyl group, a phenyl group substituted by an alkyl group having 1 to 8 carbon atoms, a phenoxy group or a phenylalkyl group with an alkyl part having 1 to 4 carbon atoms; $R_4$ denotes a hydrogen or chlorine atom, a hydroxyl group or an alkoxyl group having 1 to 4 carbon atoms; and $R_5$ denotes a hydrogen atom, an alkyl group having 1 to 12 carbon atoms or a phenylalkyl group with an alkyl part having 1 to 4 carbon atoms) comprises reduction with hydrogen of o-nitroazobenzene derivatives expressed by Formula II:

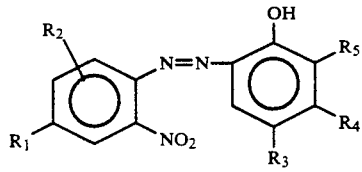

(wherein $R_1$, $R_2$, $R_3$, $R_4$ and $R_5$ each denote the same as in Formula I), the reduction being effected in a solvent containing water.

6 Claims, No Drawings

METHOD OF PREPARING 2-PHENYL BENZOTRIAZOLES

This application is a continuation of application Ser. No. 07/561,354, filed Aug. 1, 1990 which is a continuation of application Ser. No. 320,992, filed Mar. 9, 1989, abandoned.

BACKGROUND OF THE INVENTION

1. Field of the Invention

The present invention relates to a method of preparing 2-phenyl benzotriazoles which are useful as ultraviolet ray absorbers in plastics, paints, oils and so on, and which are expressed by the following formula I:

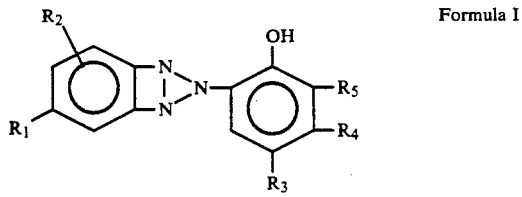

Formula I (wherein $R_1$ denotes a hydrogen atom, a chlorine atom, a lower alkyl group having 1 to 4 carbon atoms, a lower alkoxyl group having 1 to 4 carbon atoms, a carboxyl group or a sulfonic acid group; $R_2$ denotes a hydrogen or chlorine atom, a lower alkyl group having 1 to 4 carbon atoms or a lower alkoxyl group having 1 to 4 carbon atoms; $R_3$ denotes a hydrogen or chlorine atom, an alkyl group having 1 to 12 carbon atoms, a lower alkoxyl group having 1 to 4 carbon atoms, a phenyl group, a phenyl group substituted by an alkyl group having 1 to 8 carbon atoms, phenoxy group or a phenylalkyl group with an alkyl part having 1 to 4 carbon atoms; $R_4$ denotes a hydrogen or chlorine atom, a hydroxyl group or an alkoxyl group having 1 to 4 carbon atoms; and $R_5$ denotes a hydrogen atom, an alkyl group having 1 to 12 carbon atoms or a phenylalkyl group with an alkyl part having 1 to 4 carbon atoms).

2. Description of the Prior Art

Such 2-phenylbenzotriazoles are generally produced by chemical or electrolytic reduction of o-nitrohydroxy azobenzenes expressed by the following formula II:

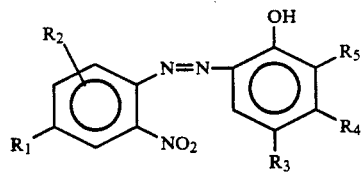

(wherein $R_1$, $R_2$, $R_3$, $R_4$ and $R_5$ each denote the same as in Formula I). Each of these conventional methods, however, has its own advantages and disadvantages, and is not always completely satisfactory. For example, Japanese Patent Publication No. 5934/1962 and U.S. Pat. No. 3,773,751 disclose a method of preparing 2-phenylbenzotriazoles in a good yield by chemically reducing o-nitroazobenzenes with zinc powder in an alcoholic sodium hydroxide solution. Such a sodium hydroxide-zinc system, however, involves the problem that it produces zinc sludge which causes contamination of waste water, and the disadvantage that the waste produced cannot easily be disposed of.

U.S. Pat. No. 2,362,988 discloses a method which uses as a reductant ammonium sulfide, an alkali sulfide, a zinc-ammonia system, a hydrogen sulfide-sodium system or a zinc-hydrochloric acid system. This method, however, has the disadvantages that a large amount of sulfite or zinc salts is produced, resulting in problems with respect to waste water contamination and difficulty of waste disposal.

Japanese Patent Laid-Open No. 133076/1981 [CA 88(26): 1971496] discloses a method which uses as a catalyst an aromatic dihydroxy compound or a quinone compound and which also requires as a reductant zinc, ammonium sulfide, an alkali metal sulfide, hydrosulfite or hydrazine. This method also has the above-described problem with respect to waste water containing metals, as well as involving problems with respect to the generation of poisonous gases from sulfide reductants and the toxicity of hydrazine itself.

Japanese Patent Laid-Open Nos. 113974/1977 [CA 88(15):197149b] and 113973/1977 [CA 88(21):105346u] disclose a method of preparing 2-phenylbenzotriazoles in a good yield by reducing the corresponding o-nitroazobenzenes with hydrogen in the presence of a hydrogenation catalyst and a basic substance. As a result of supplementary studies, however, it has been found that many kinds of impurities are produced in small amounts and cannot be removed by washing the reaction product with methanol and then recrystallizing it with ethanol. This method therefore has the problem that the 2-phenylbenzotriazoles produced by this method are inferior to those available at present in terms of both quality and cost. Particularly, Japanese Patent Laid-Open No. 113974/1977 [CA 88(15):105347p] discloses that it is preferable to mix a hydrophilic solvent with an aromatic hydrocarbon solvent because the water produced by the reaction is dissolved, but discloses no idea that water is positively mixed in a solvent system.

Japanese Patent Laid-Open No. [CA 102(5):45959K] and Japanese Patent Laid-Open No. [CA 102(5):45959K] which are related to this application disclose methods of reducing o-nitroazobenzene derivatives expressed by FormulaII with alcohols in basic catalysts using quinones and aromatic ketones, respectively. These methods are excellent methods which can resolve the problems described above with respect to air pollution and waste water contamination, but they still involve the following disadvantages:

The method disclosed in Japanese Patent Laid-Open No. [CA 109(19):170439m] which uses aromatic ketones as catalysts exhibits a good yield with the expensive catalyst used but is unsuitable for large-scale production on an industrial scale because heat is rapidly generated during the course of the reaction. The method disclosed in Japanese Patent Laid-Open No. [CA 102(5):45959K] which uses quinones as catalysts exhibits a relatively good yield but higher costs are involved because the quinones used as catalysts deteriorate and cannot be recovered. This method is also unsuitable for use as an additive in colorless plastics because the resulting products would become strongly tinged with yellow. This tendency is particularly strong in the case where $R_3$ in Formula II is an alkyl group and $R_1$, $R_2$, $R_4$ and $R_5$ are each a hydrogen atom.

The applicant has also proposed in Japanese Patent Laid-Open No. [CA 109(19):170439n] that o-nitroazobenzenes can be reduced with primary alcohol or secondary alcohol, but mentioned nothing about a method for reducing with hydrogen.

The applicant has further proposed a method of preparing 2-phenylbenzotriazoles expressed by Formula I by reducing 2-phenylbenzotriazole-N-oxides or o-nitroazobenzenes of Formula II in the following manner:

(1) reduction with an aldehyde in the presence of an aromatic ketone compound and a base (Japanese Patent-Laid Open No. 215378/1986[CA 106(21)176394e]);

(2) reduction with a primary or secondary alcohol in the presence of a catalyst comprising an aromatic ketone compound together with a basic compound (Japanese Patent Laid-Open No. [CA 109(19):170439m], U.S. Pat. No. 4,780,541); or (3) electrolytic reduction in the presence of an alkali metal hydroxide in water or a mixture of water and alcohol (Japanese Patent Laid-Open No. 186886/1988[CA 110(6):47417w]).

The applicant has also proposed a method for preparing 2-phenylbenzotriazole expressed by the above-described Formula I by reducing the 2-phenylbenzotriazole-N-oxides with an aldehyde in the presence of a catalyst comprising an aromatic ketone compound with a basic compound (Japanese Patent Laid-Open No. 215379/1986, U.S. Pat. No. 4,780,541).

SUMMARY OF THE INVENTION

It is an object of the present invention to provide a method of preparing 2-phenylbenzotriazoles which can resolve all the problems involved by the prior art.

It is another object of the present invention to provide reaction products which allow 2-phenylbenzotriazoles to be easily isolated and purified as target products by simple reduction with hydrogen.

The inventors therefore have conducted various investigations with a view to resolving the above-described problems of conventional methods of preparing 2-phenylbenzotriazoles, and particularly endeavored to develop a catalyst which can be easily handled and does not much deteriorate. As a result, it has been found that the target substances expressed by Formula I can be produced by reducing o-nitroazobenzene derivatives expressed by Formula II with hydrogen in the presence of a basic substance in an organic solvent containing water, with technical and economical advantages and no problem with respect to environmental pollution.

That is, the present invention relates to a method of preparing 2-phenylbenzotriazoles by reducing o-nitroazobenzenes with hydrogen in a solvent containing water. The present invention particularly relates to a method of preparing 2-phenylbenzotriazoles by contact-reducing o-nitroazobenzene derivatives with hydrogen in the presence of a hydrogenation catalyst and a basic substance in a solvent mixture comprising water and at least one organic solvent selected from the group consisting of alcohols, cyclic ethers, aromatic hydrocarbons and the like.

DETAILED EXPLANTION OF THE INVENTION

The form of an example of the present invention is given below.

An o-nitroazobenzene derivative which is selected as a starting material is dissolved in a solvent contained in a reaction vessel into which water, a hydrogenation catalyst and a basic substance are then placed. After the air in the reaction vessel has been replaced by hydrogen, a given amount of hydrogen is charged into the reaction vessel, and the reaction is then allowed to proceed under atmospheric pressure or a given pressure at a temperature of room temperature to 170° C. under agitation. After the reaction has been completed, the catalyst is filtered off, the solvent layer is washed with water, and the solvent is distilled off. The crude product is then purified by recrystallization to obtain the corresponding 2-phenylbenzotriazole as a pure product.

Examples of compounds expressed by Formula II that may be used as raw materials in the present invention include the following:

2-nitro-4-chloro-2'-hydroxy-3'-t-butyl-5'-methylazobenzene
2-nitro-2'-hydroxy-5'-methylazobenzene
2-nitro-2'-hydroxy-5'-t-octylazobenzene
2-nitro-2'-hydroxy-5'-t-butylazobenzene
2-nitro-4-chloro-2'-hydroxy-3',5'-di-t-butylazobenzene
2-nitro-2'-hydroxy-3',5'-di-t-amylazobenzene
2-nitro-2'-hydroxy-3',5'-di-t-butylazobenzene
2-nitro-2'-hydroxy-3'-t-butyl-5'-methylazobenzene
2-nitro-2',4'-dihydroxyazobenzene
2-nitro-4-chloro-2',4'-dihydroxyazobenzene
2-nitro-2'-hydroxy-4'-methoxyazobenzene
2-nitro-4-chloro-2'-hydroxy-3',5'-di-t-amylazobenzene
2-nitro-2'-hydroxy-5'-t-amylazobenzene
2-nitro-4-chloro-2'-hydroxy-5'-t-amylazobenzene
2-nitro-2'-hydroxy-3',5'-di(α,α-dimethylbenzyl)azobenzene
2-nitro-4-chloro-2'-hydroxy-3',5'-di-(α,α-dimethylbenzyl)azobenzene
2-nitro-2'-hydroxy-3'-αmethylbenzyl-5'-methylazobenzene
2-nitro-4-chloro-2'-hydroxy-3'-α-methylbenzyl-5'-methylazobenzene
2-nitro-2'-hydroxy-5'-n-dodecylazobenzene
2-nitro-4-chloro-2'-hydroxy-5'-n-dodecylazobenzene
2-nitro-2'-hydroxy-3',5'-di-t-octylazobenzene
2-nitro-4-chloro-2'-hydroxy-3',5'-di-t-octylazobenzene
2-nitro-4-chloro-2'-hydroxy-5'-t-octylazobenzene
2-nitro-4-methyl-2'-hydroxy-5'-methylazobenzene
2-nitro-4-methyl-2'-hydroxy-3'-t-butyl-5-methylazobenzene
2-nitro-4-n-butyl-2'-hydroxy-3',5'-di-t-butylazobenzene
2-nitro-4-n-butyl-2'-hydroxy-3'-sec-butyl-5'-t-butylazobenzene
2-nitro-4-t-butyl-2'-hydroxy-3'-sec-butyl-5'-t-butylazobenzene
2-nitro-4,6-dichloro-2'-hydroxy-5'-t-butylazobenzene
2-nitro-4,6-dichloro-2'-hydroxy-3',5'-di-t-butylazobenzene
2-nitro-4-carboxy-2'-hydroxy-5'-methylazobenzene Examples of hydrogenation catalysts that may be used in the present invention include Raney nickel, platinum oxide, platinum carbon, palladium carbon, ruthenium carbon, rhodium carbon and the like.

Examples of basic substances used in the present invention include hydroxides and carbonates of alkali metals; hydroxides and carbonates of alkali earth metals; alkyl amines such as methylamine, ethylamine, propylamine, dimethylamine, diethylamine, dibutylamine, triethylamine and tributylamine; polyalkylenepolyamines such as diethylenetriamine, triethylenetetramine, dipropylenetriamine and tripropylenetetramine; alkanolamines such as monoethanolamine, monopropanolamine, diethanolamine, dipropanolamine, triethanolamine and tripropanolamine; aromatic amines such as aniline, tolylamine and methylcyclohexylamine; heterocyclic amines such as pyridine, piperazine, triethylenediamine, diazabicyclononene, diazabicycloundecene, and the like.

Examples of organic solvents that may be used in the present invention include aromatic hydrocarbons such as benzene, toluene, xylene and the like; alcohols such as methanol, ethanol, n-propanol, n-butanol, isobutanol, n-amyl alcohol, isoamyl alcohol, sec-butanol, isopropyl alcohol and the like; and cyclic ethers such as dioxane, tetrahydrofuran and the like.

Although the amount of the hydrogenation catalyst used in the present invention depends upon the type thereof, it is generally 20 wt % or less, preferably about 0.1 wt % or more, of the weight of the compound expressed by Formula II. The amount of the basic substance used is preferably 3 to 40 wt % of the weight of the o-nitroazobenzene used expressed by Formula II. The amount of the reaction solvent used may be about 40 times or less, preferably about twice or more, the weight of the substance to be reduced expressed by Formula II. The amount of the water added is 0.2 to 35 times the weight of the substance to be reduced. The mixing ratio between the organic solvent and water is generally 1:2 to 50:1 by volume, preferably 1:1 to 4:1 by volume. The reaction temperature is room temperature to about 170° C., preferably about 15° to 70° C. The pressure of hydrogen is normal pressure to about 20 kg/cm$^2$.

Typical examples of benzotriazole compounds obtained in the present invention are expressed by Formula I. Examples of such compounds include the following:

2-(2'-hydroxy-3'-t-butyl-5'-methylphenyl)-5-chlorobenzotriazole
2-(2'-hydroxy-3',5'-di-t-butylphenyl)-5-chlorobenzotriazole
2-(2'-hydroxy-3',5'-di-t-amylphenyl)benzotriazole
2-(2'-hydroxy-5'-methylphenyl)benzotriazole
2-(2'-hydroxy-5'-t-butylphenyl)benzotriazole
2-(2'-hydroxy-5't-octylphenyl)benzotriazole
2-(2'-hydroxy-3',5'-di-t-butylphenyl)benzotriazole
2-(2'-hydroxy-3'-t-butyl-5'-methylphenyl)benzotriazole
2-(2',4'-dihydroxyphenyl)benzotriazole
2-(2'-hydroxy-4'-methoxyphenyl)benzotriazole
2-[2'-hydroxy-3',5'-di(α,α-dimethylbenzyl)phenyl]benzotriazole
2-(2'-hydroxy-3'-α-methylbenzyl-5'-methylphenyl) benzotriazole, and the like.

The present invention enables 2-phenylbenzotriazoles to be produced in a good yield by reduction with hydrogen of o-nitroazobenzene derivatives expressed by Formula II which are selected as starting materials, with producing small amounts of side reaction products, and enables the target products to be simply isolated and purified, as well as having an excellent effect in that no problem occurs with respect to environmental pollution such as air pollution, waste water contamination and the like.

DESCRIPTION OF THE PREFERRED EMBODIMENTS

The present invention is further illustrated by the following Examples concerning preparation and usage, but should not be limited thereto.

EXAMPLE 1

38.39 g (0.1 mol) of 2-nitro-2'-hydroxy-3',5'-di-t-amylazobenzene, 5 g of Raney nickel, 100 ml of toluene, 100 ml of isopropyl alcohol (referred to as "IPA" hereinafter) 100 ml of water and 8 g (0.2 mol) of caustic soda were charged into a 500-ml stainless autoclave with an agitator. After the air in the flask had been replaced by hydrogen, the pressure of hydrogen was set to 10 kg/cm$^2$. The temperature was increased at a rate of 20° to 40° C./hour and then 40° to 50° C./hour while the resultant mixture being agitated. Reaction was then effected at 50° to 90° C. for 2 hours and then 90° C. for 7 hours and was stopped when no more hydrogen was absorbed by the reaction solution. The autoclave was cooled, and the catalyst was filtered off. After the filtrate had been allowed to stand, the toluene layer was separated, and most part of the toluene was distilled off. The residual solid obtained was crystallized by IPA and the dried to obtain 28.8 g of 2-(2'-hydroxy-3',5'-di-t-amylphenyl)benzotriazole (yield, 82%; melting point, 79° to 80° C.).

EXAMPLE 2

35.5 g (0.1 mol) of 2-nitro-2'-hydroxy-5'-t-octylazobenzene, 0.125 g of 5% palladium carbon, 100 ml of toluene, 100 ml of IPA, 50 ml of water and 7 g of 50% dimethylamine were charged into a 500-ml stainless autoclave with an agitator. Reaction was effected in the same way as that employed in Example 1 and stopped when no more hydrogen was absorbed by the reaction solution. After the reaction had been completed, after treatment was performed in the same way as in Example 1 to obtain 26.8 g of 2-(2'-hydroxy-5'-t-octylphenyl)benzotriazole (yield, 82.9%; melting point, 103° to 105° C.).

EXAMPLE 3

35.5 g (0.1 mol) of 2-nitro-2'-hydroxy-3',5'-di-t-butylazobenzene, 0.125 g of 5% palladium carbon, 100 ml of toluene, 100 ml of IPA, 100 ml water and 8.3 g of caustic soda were charged into a 500-ml stainless autoclave equipped with an agitator. After the air in the autoclave had been replaced by hydrogen, the pressure of hydrogen was set to 10 kg/cm$^2$. Reaction was effected in the same way as that employed in Example 1. After the reaction had been completed, the catalyst was filtered off. When part of the filtrate was subjected to quantitative analysis using GC, it was found that the yield of 2-(2'-hydroxy-3',5'-di-t-butylphenyl)benzotriazole is 82%. After the solvent had been distilled off from the filtrate, the residual solid was crystallized by IPA, washed with IPA and then dried to obtain 23.6 g of 2-(2'-hydroxy-3',5'-di-t-butylphenyl)benzotriazole (yield, 73%; melting point, 150° to 152° C.).

EXAMPLE 4

25.7 g (0.1 mol) of 2-nitro-2'-hydroxy-5'-methylazobenzene, 0.125 g of palladium carbon, 100 ml of toluene, 50 ml of IPA, 25 ml of water and 7 g of 50% dimethylamine were charged into a 500-ml stainless autoclave with an agitator. After the air in the flask had been replaced by hydrogen, the pressure of hydrogen was set to 10 kg/cm$^2$. Reaction was then effected in the same way as that employed in Example 1. After the reaction had been completed, the catalyst was filtered off, and part of the filtrate was subjected to quantitative analysis using gas chromatography (GC). The results revealed a yield of 81% of 2-(2'-hydroxy-5'-methylphenyl)benzotriazole. The toluene layer was separated, and most part of toluene was then distilled off from the layer. The residual solid was then crystallized using ethanol and then dried to obtain 15.7 g of 2-(2'-hydroxy-5'-methylphenyl)benzotriazole (yield, 69.8%; melting point, 128° to 130° C.).

EXAMPLE 5

39.0 g (0.1 mol) of 2-nitro-4-chloro-2'-hydroxy-3',5'-di-t-butylazobenzene, 0.125 g of 5% palladium carbon, 100 ml of toluene, 60 ml of 2-butanol, 120 ml of water and 7 g of tributylamine were charged into a 500-ml stainless autoclave with an agitator. Reaction was effected in the same manner as that employed in Example 1. After the reaction had been completed, after treatment was performed in the same way as that employed in Example 1 to obtain 28.1 g of 2-(2'-hydroxy-3',5'-di-t-butylphenyl)-5-chlorbenzotriazole(yield, 78.6%; melting point, 152° to 153° C.).

What we claim is:

1. A method of preparing 2-phenylbenzotriazoles of Formula I:

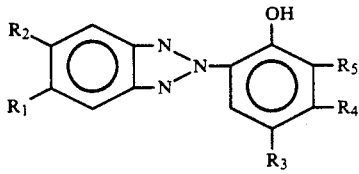

wherein
$R_1$ is hydrogen or chlorine, a $C_1$-$C_4$ alkyl, a $C_1$-$C_4$ alkoxyl, a carboxyl group or a sulfonic acid group;
$R_2$ is hydrogen or chlorine, a $C_1$-$C_4$ alkyl or a $C_1$-$C_4$ alkoxyl;
$R_3$ is hydrogen of chlorine, a $C_1$-$C_{12}$ alkyl, a $C_1$-$C_{12}$ alkoxyl, a phenyl group, a phenyl group substituted by a $C_1$-$C_8$ alkyl, a phenoxy group or a phenylalkyl group with a $C_1$-$C_4$ alkyl;
$R_4$ is hydrogen of chlorine, a hydroxyl group or a $C_1$-$C_4$ alkoxyl; and
$R_5$ is hydrogen, a $C_1$-$C_{12}$ alkyl or a phenylalkyl group with a $C_1$-$C_4$ alkyl part consisting of reducing, with hydrogen, o-nitroazobenzene compounds of Formula II:

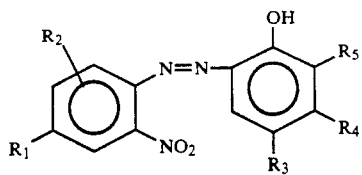

wherein $R_1$, $R_2$, $R_3$, $R_4$ and $R_5$ each denotes the same as in said Formula I, and effecting said reduction in the presence of added water and an organic solvent in a ratio range of 2:1 to 1:50 by volume wherein the amount of water added is 14–70 times the moles of the substance to be reduced, and in the presence of an organic amine selected from the group consisting of methylamine, ethylamine, propylamine, dimethylamine, diethylamine, dibutylamine, triethylamine, tributylamine, diethylenetriamine, triethylenetetramine, dipropylenetriamine and tripropylenetetramine, monoethanolamine, monopropanolamine, diethanolamine, dipropanolamine, triethanolamine, tripropanolamine, aniline, tolylamine, methylcyclohexylamine, pyridine, piperazine, triethylenediamine and diazabicyclononene,
wherein said reduction further consists of using a palladium carbon hydrogenation catalyst.

2. The method of claim 1, further consisting of effecting said reduction in a system consisting essentially of water and an organic solvent selected from the group consisting of aromatic hydrocarbons, alcohols and cyclic ethers at a pressure of hydrogen in a range of normal pressure to 20 kg/cm² in the presence of a hydrogenation catalyst and an organic amine.

3. The method of claim 1, further consisting essentially of effecting said reduction in a temperature range of room temperature to 170° C.

4. The method of claim 2, further consisting of using as the amount of said organic amine not less than about 0.1% by weight of the o-nitroazobenzene compound used as a starting material.

5. The method of claim 1 wherein the mixing ratio of the organic solvent and water is in the range of 1:1 to 4:1 by volume.

6. The method of claim 1 or 2 wherein the organic amine is diethylamine or tributylamine.

* * * * *

UNITED STATES PATENT AND TRADEMARK OFFICE
CERTIFICATE OF CORRECTION

PATENT NO. : 5,187,289　　　　　　　　　　　　　Page 1 of 2
DATED : February 16, 1993
INVENTOR(S) : Naohiko Fukuoka, et al.

It is certified that error appears in the above-indentified patent and that said Letters Patent is hereby corrected as shown below:

| | |
|---|---|
| Col. 2, line 8: | delete "1971496" and insert -- 197149b --. |
| Col. 2, line 18: | after "CA 88(15)" delete "197149b " and insert -- 105347p --. |
| Col. 2, line 38: | after "Laid-Open No." insert -- 170172/1984 --. |
| Col. 2, line 39: | after "Laid-Open No." delete "CA 102(5):45959K" and insert -- 72682/1988 CA 109(19):170439m --. |
| Col. 2, line 54: | after "Laid-Open No." insert -- 170172/1984 --. |
| Col. 2, line 65: | after "Laid-Open No." insert -- 72683/1988 -- and after "170439" delete "n" and insert -- m --. |

UNITED STATES PATENT AND TRADEMARK OFFICE
CERTIFICATE OF CORRECTION

PATENT NO. : 5,187,289
DATED : February 16, 1993
INVENTOR(S) : Naohiko Fukuoka, et al.

It is certified that error appears in the above-indentified patent and that said Letters Patent is hereby corrected as shown below:

Col. 3, line 13: after "Laid-Open No." insert --72683/1988--.

Signed and Sealed this

Thirtieth Day of August, 1994

Attest:

BRUCE LEHMAN

*Attesting Officer*   *Commissioner of Patents and Trademarks*